(12) United States Patent
Cassidy

(10) Patent No.: US 8,222,768 B2
(45) Date of Patent: Jul. 17, 2012

(54) METHODS AND APPARATUS FOR POWERING ELECTRIC DEVICES COUPLED TO A PATIENT TO REDUCE TRANSIENTS IN PATIENT MONITORING DEVICES

(75) Inventor: David Ellsworth Cassidy, Chelmsford, MA (US)

(73) Assignee: General Electric Company, Schenectady, NY (US)

( * ) Notice: Subject to any disclaimer, the term of this patent is extended or adjusted under 35 U.S.C. 154(b) by 311 days.

(21) Appl. No.: 12/684,487

(22) Filed: Jan. 8, 2010

(65) Prior Publication Data
US 2011/0169343 A1    Jul. 14, 2011

(51) Int. Cl.
*H02J 1/00* (2006.01)
*H02J 3/00* (2006.01)

(52) U.S. Cl. ......................................................... 307/86
(58) Field of Classification Search .................. 307/86
See application file for complete search history.

(56) References Cited

U.S. PATENT DOCUMENTS

| | | | | |
|---|---|---|---|---|
| 3,293,631 A | * | 12/1966 | Premack | 340/552 |
| 5,002,063 A | | 3/1991 | Haner | |
| 6,296,936 B1 | * | 10/2001 | Yahiaoui et al. | 428/378 |
| 7,598,706 B2 | * | 10/2009 | Koski et al. | 320/117 |
| 2007/0087703 A1 | | 4/2007 | Li et al. | |
| 2007/0149162 A1 | * | 6/2007 | Greene et al. | 455/343.1 |
| 2008/0009847 A1 | * | 1/2008 | Ricart et al. | 606/32 |

FOREIGN PATENT DOCUMENTS

WO    97/06728 A1    2/1997

OTHER PUBLICATIONS

GB Search Report from corresponding GB Application No. GB1021818.8 on Mar. 4, 2011.

* cited by examiner

*Primary Examiner* — Rexford Barnie
*Assistant Examiner* — Toan Vu
(74) *Attorney, Agent, or Firm* — Alan Taboada; Moser Taboada

(57) ABSTRACT

Apparatus, systems, and methods for powering an electric device coupled to a patient to reduce transients on patient monitoring devices are provided herein. In some embodiments, an apparatus for reducing transient electrical events on a patient monitoring device may include a device that can be powered on or off to cause current flow through a load of the device and which has a line out that is capacitively coupled to a patient during use; and a control circuit to control a periodic coupling of first and second voltage sources to the load out of phase at a predetermined carrier frequency to provide continuous current flow through the load in alternating directions, and to control the periodic coupling of first and second voltage sources to the load in phase at a predetermined carrier frequency to provide no current flow through the load.

23 Claims, 5 Drawing Sheets

METHODS AND APPARATUS FOR POWERING ELECTRIC DEVICES COUPLED TO A PATIENT TO REDUCE TRANSIENTS IN PATIENT MONITORING DEVICES

FIELD

Embodiments of the present invention generally relate to electrical devices coupled to a patient being monitored with a patient monitoring device and, more particularly, to methods and apparatus for reducing transients on patient monitoring devices.

BACKGROUND

Many electrical devices are powered by passing a current through a load. A non-limiting example of such a device is a resistive heater attached to an intravenous (IV) liquid dispenser such as the ENFLOW® IV Fluid/Blood Warmer available from Vital Signs, Inc., located in Totowa, N.J. The resistive heater heats an IV fluid line by passing a current through a heating coil disposed proximate the IV fluid line. As the current passes through the coil, the temperature of the coil rises, heating an attached cartridge containing the IV fluid line.

Many common medical monitoring devices measure patient vital signs by monitoring low frequency electrical signals measured by various leads attached to the patient. The typical input to these monitoring devices is a low-pass filter. The low-pass filter is typically constructed of some combination of passive components such as resistors, capacitors, and inductors.

The inventor has observed that, in some instances, when a device, such as an IV fluid warmer or other electrical device, is coupled to a patient that is being monitored by a monitoring device as discussed above, transients generated when powering the device on or off may be undesirably picked up and displayed by the patient monitoring device. The inventor believes that this is due to a capacitive coupling of the electric device to the patient that facilitates transmission of the transients generated by powering the device on or off. For example, when an IV fluid warmer is powered on or off, transients are generated that travel through the IV fluid line via a capacitive coupling of the resistive heating element to the IV fluid line. Although these transients are generally short-lived, the inventor believes that transients that occur at low frequencies are filtered by the low-pass filter into lower amplitude rising signals that are visible on patient monitoring devices as the signals fall within the pass band of the physiological signals. As such, these low frequency signals are then measured by the patient monitoring device, resulting in erroneous data. Such erroneous data makes monitoring patient vital signs difficult for doctors and nurses and may cause false-alarms in the monitoring equipment. While shielding within the input of the patient monitoring device may block high frequency transients, such filtering is ineffective at blocking signals within the low frequency pass-band of signals allowed by the monitoring device.

As such, the inventor has provided an apparatus and system for powering electric devices coupled to a patient that reduces transients on patient monitoring devices.

SUMMARY

Apparatus, systems, and methods for powering an electric device coupled to a patient to reduce transients on patient monitoring devices are provided herein. In some embodiments, an apparatus for reducing transient electrical events on a patient monitoring device may include a device that can be powered on or off to cause current flow through a load of the device and which has a line out that is capacitively coupled to a patient during use; and a control circuit to control the periodic coupling of first and second voltage sources to the load out of phase at a predetermined carrier frequency to provide continuous current flow through the load in alternating directions, and to control the periodic coupling of first and second voltage sources to the load in phase at a predetermined carrier frequency to provide no current flow through the load.

In some embodiments, an apparatus for reducing transient electrical events on a patient monitoring device may include a device that can be powered on or off to cause current flow through a load of the device and which is capacitively coupled to a patient during use; a first voltage source coupled to a first side of the device through a first switching block; a second voltage source coupled to a second side the device opposite the first through a second switching block; and a controller to control the periodic coupling of the first and the second voltage sources to the load out of phase at a predetermined carrier frequency to provide continuous current flow through the load in alternating directions, and to control the periodic coupling of first and second voltage sources to the load in phase at a predetermined carrier frequency to provide no current flow through the load.

In some embodiments, a method for reducing transients on patient monitoring devices when powering a device having a load that is capacitively coupled to a patient monitoring device may include periodically coupling a first and a second voltage source to the device out of phase at a predetermined carrier frequency to provide continuous current flow through the load in alternating directions; and periodically coupling the first and the second voltage sources to the device in phase at a predetermined carrier frequency to provide no current flow through the load.

Other and further embodiments of the present invention are described below.

BRIEF DESCRIPTION OF THE DRAWINGS

Embodiments of the present invention, briefly summarized above and discussed in greater detail below, can be understood by reference to the illustrative embodiments of the invention depicted in the appended drawings. It is to be noted, however, that the appended drawings illustrate only typical embodiments of this invention and are therefore not to be considered limiting of its scope, for the invention may admit to other equally effective embodiments.

Figure 1:
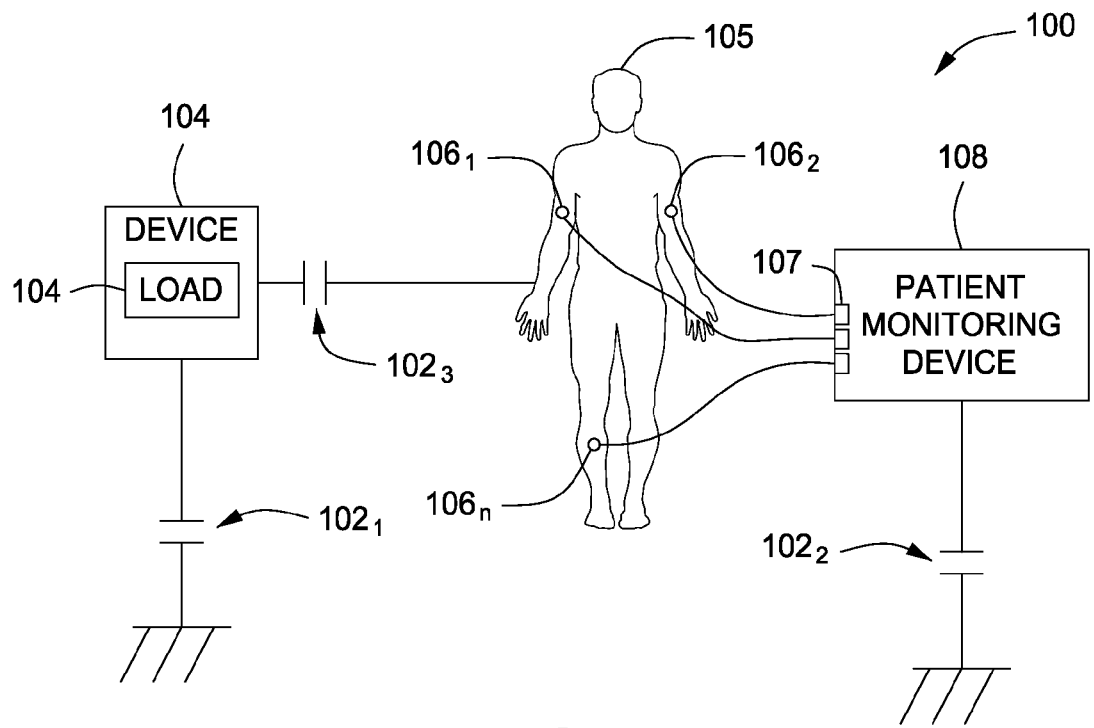
FIG. 1 is a block diagram of a device having a load that is capacitively coupled to a patient in accordance with some embodiments of the present invention.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION

Apparatus, systems, and methods for powering an electric device coupled to a patient to reduce transients on patient monitoring devices are described herein. The inventive apparatus advantageously reduces or eliminates low frequency electrical transients generated by a device that may be transmitted along an input that is capacitively coupled to a patient. Such low frequency electrical transients would normally pass through a low-pass filter on a monitoring device connected to the patient. The transients may then undesirably register on the monitoring device as erroneous data.

The present invention may be utilized to advantage in numerous devices commonly used in conjunction with monitoring devices. FIG. 1 depicts an illustrative system including an electric device 104 having a load 103 that is capacitively coupled to a patient 105. The patient 105 is monitored by a patient monitoring device 108 via one or more electrodes 106 ($106_{1-n}$ shown in FIG. 1) coupled to the patient 105 and the patient monitoring device 108. Each electrode 106 may be coupled to a low-pass filter 107 at the input of the patient warming device 108. Non-limiting examples of suitable devices 104 include the ENFLOW® IV Fluid Warmer produced by Vital Signs Inc., bypass pumps, infusion pumps, warming blankets, and any other device with a large enough footprint to have a high capacitive coupling to a patient. Non-limiting examples of suitable patient monitoring devices 108 include neuromonitors, electro-cardiogram monitors, sleep diagnostic monitors, and any other device that displays signals that can be interfered with by a capacitive coupling with the patient as described herein.

The patient monitoring device 108 and device 104 receive power from one or more power sources (not shown in FIG. 1) and may be capacitively coupled to ground via the power source, as schematically depicted by capacitors $102_1$ and $102_2$. The device 104 is also capacitively coupled to the patient 106, as schematically depicted by the capacitor $102_3$. In one specific example, the device may be an intravenous (IV) liquid heater capacitively coupled to the patient by way of an IV line. When the IV liquid heater is powered on, transients travel through the IV fluid receptacle, down the IV line, and into the patient. The transients may then register on the patient monitoring device 108, resulting in erroneous data.

Figure 1A:
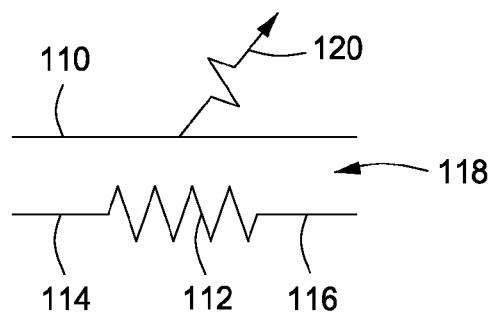
FIG. 1A is an illustrative schematic diagram of a capacitive coupling of a device showing transients that may be generated when the device is powered on and off.

For example, FIG. 1A is a schematic illustration of a capacitive coupling within a device, as described above. In some embodiments, the device includes a fluid cartridge 110 and a resistive heat coil 112 disposed proximate the fluid cartridge 110 to efficiently transfer heat thereto during operation. The resistive heat coil 112 has a first end 114 and a second end 116 that may each be coupled to a power source and ground to facilitate flowing current through the resistive heat coil 112, as described in more detail below. As current flows through the resistive heat coil 112, the temperature of the coil 112 rises, heating the fluid cartridge 110. The intervening dielectric materials disposed between the opposing surfaces of the fluid cartridge 110 and the heating coil 112 creates a dielectric interface 118 that functions as a capacitor. When the device is initially powered on, the capacitor discharge, generating low frequency transients 120 through the fluid cartridge 110. Since the fluid cartridge 110 is coupled to a patient, the transients 120 may travel through the patient. In instances where the present invention is not utilized, such transients may affect any monitoring devices that are also coupled to the patient. While the preceding example describes a device having a resistive load, the teachings provided herein are applicable to devices featuring other types of loads, such as inductive loads, capacitive loads, motor loads, lamp loads, and the like.

Figure 2:
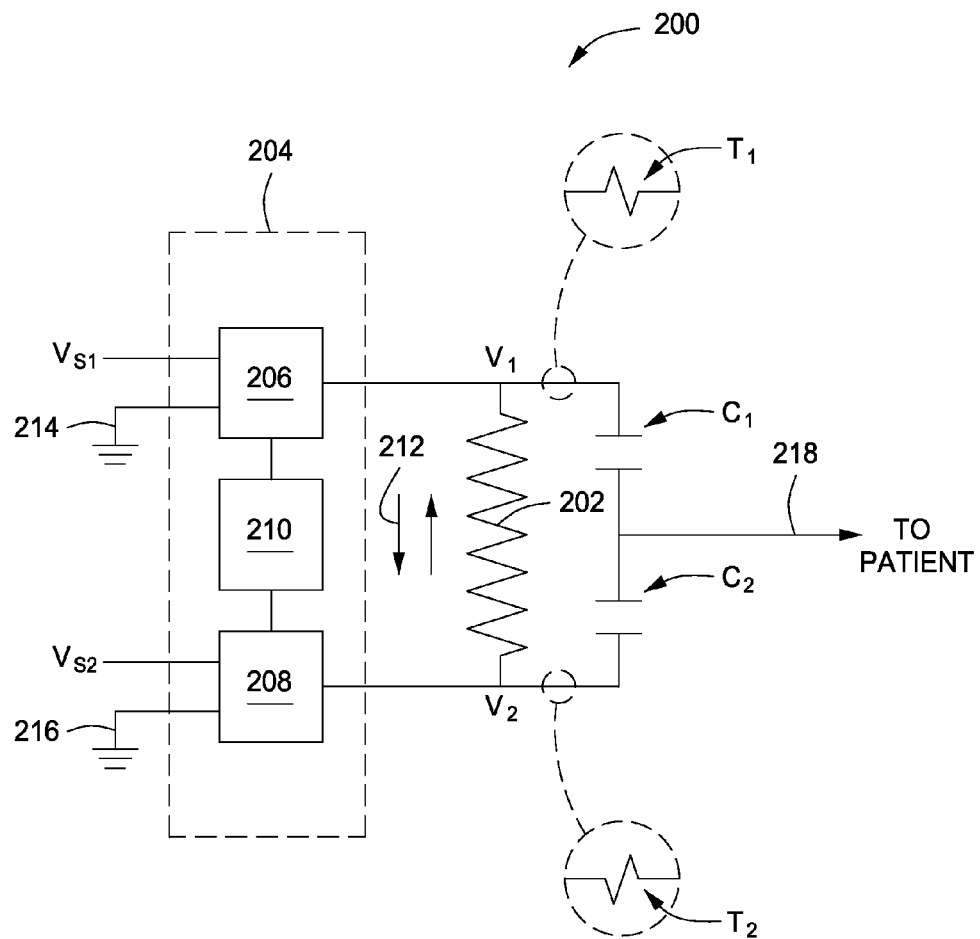
FIG. 2 is a schematic diagram of a device control circuit in accordance with some embodiments of the present invention.

FIG. 2 is a schematic diagram of a system 200 in accordance with some embodiments of the present invention. The system 200 includes a device including a load 202, such as any of the devices discussed above with respect to FIG. 1, coupled to a control circuit 204. As noted above, the resistive load in the present example is illustrative only, and teachings provided herein may be applied to other types of loads, such as capacitive loads, inductive loads, motor loads, lamp loads, and the like, and combinations thereof. The control circuit 204 includes a first switching block 206, a second switching block 208, and a controller 210 to control the operation of the first and second switching blocks. In some embodiments, a separate controller may be provided within or coupled to each switching block to independently control the operation thereof in accordance with the teachings provided herein.

The first switching block 206 may be coupled to a first voltage source $V_{s1}$ and a first ground 214. The second switching block 208 may be coupled to a second voltage source $V_{s2}$ and a second ground 216. The first and second voltage sources may be any suitable voltage source, such as one or more DC power supplies. In some embodiments, the first and second voltage sources may be provided by a single voltage generator, where connections of the positive and ground terminals across the load may be controlled as described herein. The controller 210 controls the operation of the first and second switching blocks such that the first and second voltage sources $V_{s1-2}$ are periodically coupled to the load 202 at a predetermined frequency (e.g., switched at a predetermined frequency, or a carrier frequency) and such that the first and second voltage sources $V_{s1-2}$ are periodically coupled to the load 202 either contemporaneously (e.g., in phase) or alternatingly (e.g., 180 degrees out of phase). The voltage sources $V_{s1-2}$ are each equal in potential and polarity. In some embodiments, the carrier frequency may be higher than the pass band of any physiological monitors coupled to the patient. In some embodiments, the carrier frequency is greater than 10 KHz and less than 20 KHz. This range of frequencies is advantageously high enough to be filtered by the low pass filter of the monitoring device and low enough to minimize electromagnetic interference. Any radiated energy from an electric/magnetic field that gets rectified by any device including body diodes of semiconductors will remain at a constant DC level.

When the first and second voltage sources $V_{s1-2}$ are periodically coupled to the load out of phase, a current may flow through the load 202 in alternating directions, as indicated by arrow 212 (e.g., corresponding to an "on" state of the device). When the first and second voltage sources $V_{s1-2}$ are periodically coupled to the load in phase, no current flows through the load 202 (e.g., corresponding to an "off" state of the device). Each period of coupling a respective voltage source to the load may include and on time and an off time which together add up to the period. In some embodiments, the on time is equal to the off time. In some embodiments, the on time and the off time, e.g., the frequency of the switching, may be the same during the in phase and the out of phase modes of operation. The period may repeated continuously while the device is coupled to a patient, or while the device is coupled to a patient in concert with a monitoring device also being coupled to the patient.

Figure 3:
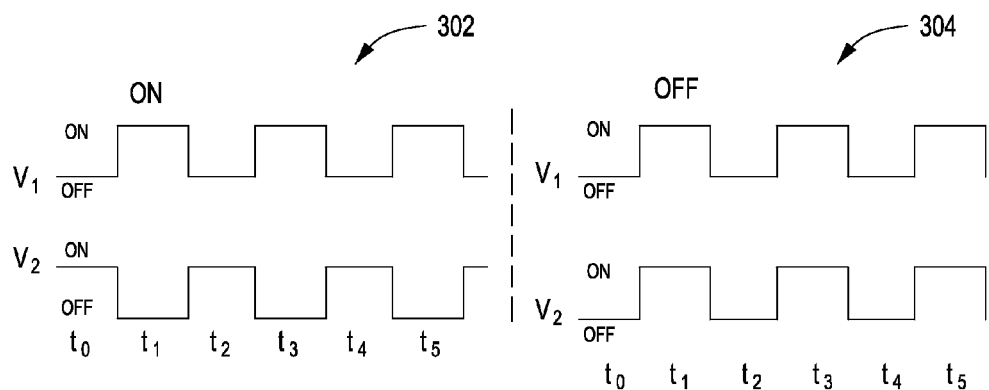
FIG. 3 is an illustrative diagram of the control of the first and second voltages over time in accordance with some embodiments of the present invention.

For example, FIG. 3 is an illustrative diagram of the control of the first and second voltages over time in accordance with some embodiments of the present invention. As shown in graph 302, when the device is to be powered on, the switching blocks are controlled to periodically couple the first and second voltage sources $V_{S1}$ and $V_{S2}$ in an out of phase manner. For example, when the first voltage source $V_{s1}$ is coupled to the load (or "on" as depicted in FIG. 3), the second voltage source $V_{S2}$ is not coupled to the load ("off" as depicted in FIG. 3), and vice-versa. This causes current to travel back and forth through the load 202, as discussed above with respect to FIG. 2.

When the device is to be powered off, the switching blocks are controlled to periodically couple the first and second voltage sources $V_{S1}$ and $V_{S2}$ in an in phase manner. For example, when the first voltage source $V_{s1}$ is coupled to the load, the second voltage source $V_{S2}$ is also coupled to the load. When the first voltage source $V_{s1}$ is not coupled to the load, the second voltage source $V_{S2}$ is also not coupled to the load. As such, the in phase switching of the first and second voltage sources results in no current flow through the load.

Returning to FIG. 2, as discussed above, the load 202 may be capacitively coupled to a patient, as depicted by line 218 and capacitors $C_1$ and $C_2$. Each time the control circuit switches the coupling to a respective voltage source in the out of phase mode of operation (i.e., the load is energized) a spike, or transient is created (as depicted by transients $T_1$ and $T_2$ in FIG. 2). However, due to the configuration of the device having a voltage source and a ground coupled to either side of the load 202, the transients $T_1$ and $T_2$ have opposing polarity and substantially simultaneously occur, thereby substantially canceling each other out and resulting in little or no voltage potential change in the line 218 coupled to the patient and no current flowing along the line 218. As such, the transients due to energizing the load are either reduced or not picked up at all by the patient physiological monitors, If the alternating current flow were to stop, de-energizing the load, a transient would be seen by the physiological monitoring device because the coupling capacitors ($C_1$ and $C_2$) would discharge and not charge again until the load was re-energized, causing a low frequency event which could be seen on monitoring device. To de-energize the load without causing a low frequency transient the switching is continued but with each side of the load being driven 0 degrees out of phase (i.e., in phase). The coupling capacitors ($C_1$ and $C_2$) will now charge and discharge and the patient node will have a very small alternating potential. Since each side of the load is driven at a carrier frequency that is greater than the pass band of the patient monitoring device, any transient generated on the line 218 is predominantly blocked by the low pass filter on the input of the monitoring device.

Figure 4:
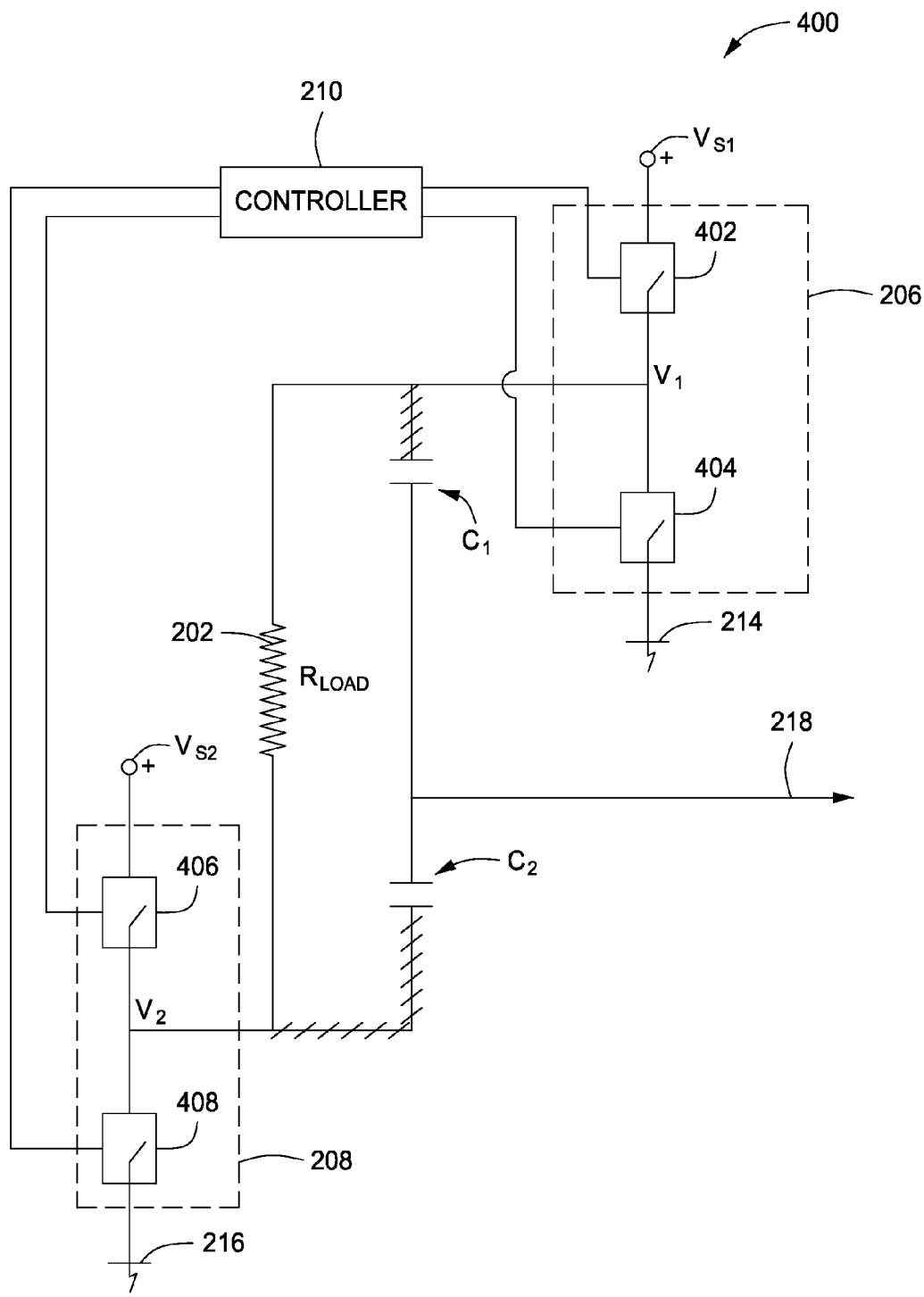
FIG. 4 is a schematic diagram of a device control circuit in accordance with some embodiments of the present invention.

FIG. 4 is a schematic diagram for a system 400 in accordance with some embodiments of the present invention. Elements depicted in FIG. 4 that are similar to those depicted in FIG. 2 are shown with the same reference numeral as shown in FIG. 2. The system 400 includes a load 202 coupled to a coupled to a control circuit 204 including a first switching block 206, a second switching block 208, and a controller 210 to control the operation of the first and second switching blocks.

In some embodiments, the first switching block 206 may include a first switch 402 and a second switch 404. The first switch 402 is coupled between the first voltage source $V_{s1}$ and the load 202. The second switch 404 is coupled between the first ground 216 and the load 202. Each of the first and second switches is coupled to the controller 210.

In some embodiments, the second switching block 208 may include a third switch 406 and a fourth switch 408. The third switch 406 is coupled between the second voltage source $V_{s2}$ and the load 202. The fourth switch 408 is coupled between the second ground 218 and the load 202. Each of the third and fourth switches is also coupled to the controller 210. Alternatively, a separate controller may be provided to control the third and fourth switches.

The switches 402, 404, 406, and 408 may be any suitable switches compatible with the use and operation as described herein.

The load 202 is a representation of the energized load portion of a device 104 as discussed with respect to FIG. 1. The load 202 is capacitively coupled to a line 218, for example, that may be coupled to a patient that also has physiological monitors coupled thereto. The capacitive coupling is shown in FIG. 3 by first and second coupling capacitors $C_1$ and $C_2$.

In operation, the controller 210 controls the operation of the four switches 402-408 via control inputs. In some embodiments, the controller 210 may be a separate hardware circuit. In some embodiments, the controller 210 may be implemented in software executed on a microcontroller present in the device 104 or otherwise provided. When the device 104 is to be powered on, the controller 210 alternates engaging each of the pairs of first switch 402 and fourth switch 408, and second switch 404 and third switch 406 to alternatingly couple the load 202 to the first voltage source $V_{s1}$ and the second ground 216 (to cause a current flow through the load in a first direction) and to the second voltage source $V_{s2}$ and the first ground 214 (to cause a current flow through the load in a second direction opposite the first).

As the pairs of switches alternate out of phase, the voltages $V_1$ and $V_2$ alternatingly rise and fall (with one or the other always present to ensure continuous flow of current through the load 202). Every time the switches alternate, the potential at the junction of the coupling capacitances (the first and second capacitors $C_1$ and $C_2$) remains at the same potential. Specifically, since the energy polarities of generated transients are constantly reversed, the transients cancel one another out and the potential of the line 218 going to the patient remains constant. Furthermore, the current passing through the load 202 remains constant and the device remains "on", even though the direction of the current is constantly reversed.

When the device 104 is to be powered off, the controller 210 alternates engaging each of the pairs of first switch 402 and third switch 406, and second switch 404 and fourth switch 408. Because there is no difference in potential between $V_1$ and $V_2$ during this mode of operation (since both sides are either ground or positive), no current flows through the load 202. Since the capacitors $C_1$ and $C_2$ are oscillating at a high frequency, any transients sent through the line 218 are filtered out by the low-pass filter on the monitoring device 108 (depicted in FIG. 1).

Figure 5:
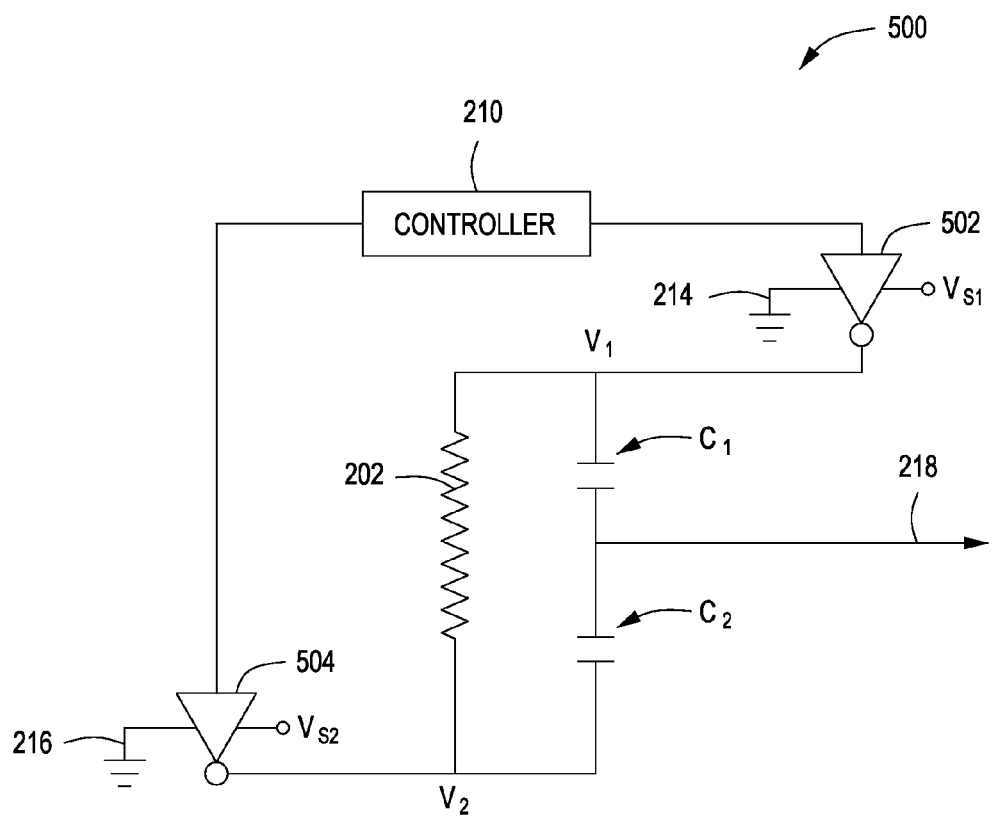
FIG. 5 is a schematic diagram of a device control circuit in accordance with some embodiments of the present invention.

FIG. 5 is a schematic diagram of a system 500 in accordance with some embodiments of the present invention. Elements depicted in FIG. 5 that are similar to those depicted in FIG. 2 are shown with the same reference numeral as shown in FIG. 2. The system 500 includes a load 202 coupled to a control circuit 204 including a first inverter 502 and a second inverter 504. The controller 210 controls the operation of the first inverter 502 and the second inverter 504 to power the device 104 on and off. When the first inverter 502 and second inverter 504 are operated out of phase (i.e., when the first inverter is operating as a source and the second inverter is operating as a sink, and vice-versa), current passes through the load 506 and the device 104 is powered on. When the first inverter 502 and the second inverter 504 are operated in phase (i.e., when the first inverter is operating as a sink and the second inverter is operating as a sink, and when the first inverter is operating as a source and the second inverter is operating as a source), no current passes through the load 506 and the device 104 is powered off. As discussed above with respect to FIG. 4, when the device 104 is powered off, the inverters oscillate with a high frequency such that the frequency is greater than the maximum allowed through the low-pass filter on the patient monitoring device 108.

Figure 6:
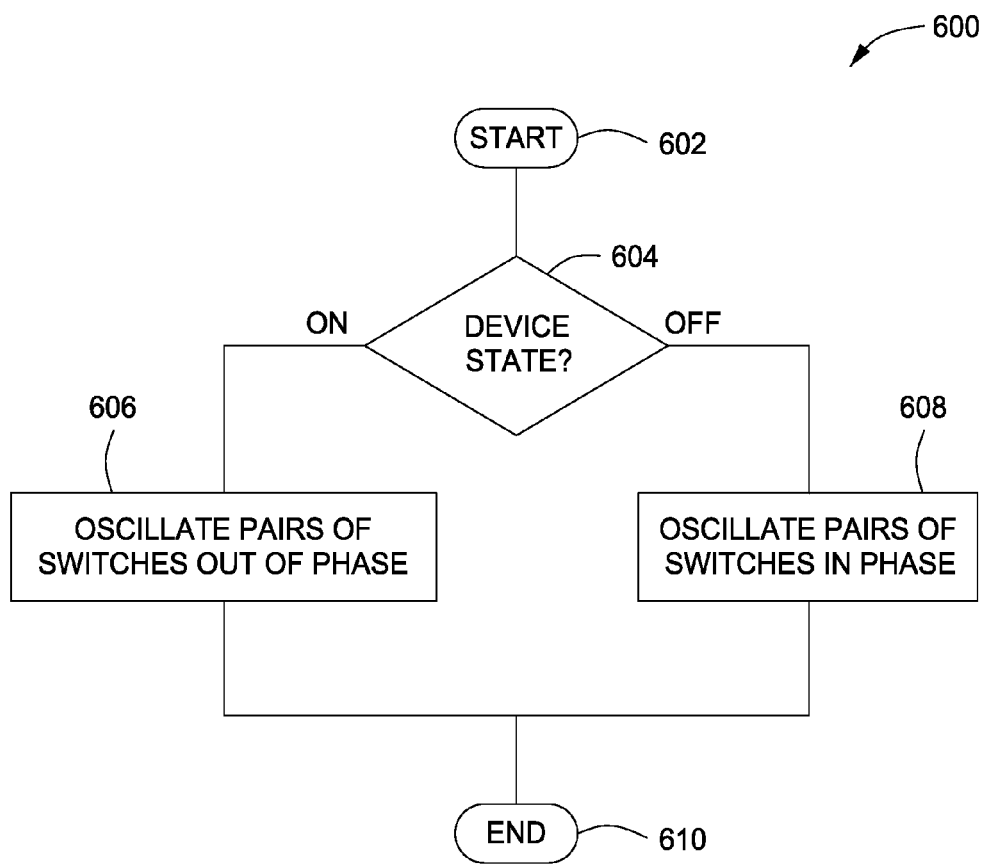
FIG. 6 is a flow diagram for a method for powering electric devices coupled to a patient to reduce transients in patient monitoring devices in accordance with some embodiments of the present invention.

FIG. 6 is a flow diagram for a method 600 for powering electric devices coupled to a patient to reduce transients in patient monitoring devices in accordance with some embodiments of the present invention. The method 600 is described with respect to the system as described in FIGS. 1 and 2. The method 600 generally begins at 602 with a device 104 capacitively coupled to a patient 106 having a patient monitoring device 108 coupled thereto. At 604, the method determines whether the device 104 should be powered on or off. If the device 104 is to be powered on, the method proceeds to 606. If the device 104 is to be powered off, the method proceeds to 608.

At 606, the method powers the device 104 on by periodically coupling the first and second voltage sources $V_{s1-2}$ to the load 202 at a predetermined frequency and in an out of phase manner, such that current alternatingly flows through the load, as discussed above.

At 608, the method powers the device off by periodically coupling the first and second voltage sources Vs1-2 to the load 202 at a predetermined frequency in an in phase manner such that current does not pass through the load. Upon completion of 606 or 608, the method generally ends at 610.

Thus, apparatus, systems, and methods for powering an electric device coupled to a patient to reduce transients on patient monitoring devices are described herein. The inventive apparatus advantageously substantially cancels electrical transients generated by a device from being transmitted to an input that is capacitively coupled to a patient, thereby reducing erroneous display of such signals by the patient monitoring device.

While the foregoing is directed to embodiments of the present invention, other and further embodiments of the invention may be devised without departing from the basic scope thereof.

The invention claimed is:

1. An apparatus for reducing transient electrical events on a patient monitoring device, comprising:
    a device that is capable of being powered on or off to cause current flow through a load of the device and which has a line out that is capacitively coupled to a patient during use; and
    a control circuit to control a periodic coupling of first and second voltage sources to the load out of phase at a predetermined carrier frequency to provide continuous current flow through the load in alternating directions, and to control the periodic coupling of first and second voltage sources to the load in phase at a predetermined carrier frequency to provide no current flow through the load.

2. The apparatus of claim 1, wherein the first voltage source and the second voltage source are provided by a single voltage generator.

3. The apparatus of claim 1, wherein the control circuit further comprises:
    a first switching block, a second switching block, and a controller to control the operation of the first and second switching blocks.

4. The apparatus of claim 3, wherein the first switching block is coupled to a first voltage source and a first ground and wherein the second switching block is coupled to a second voltage source and a second ground.

5. The apparatus of claim 4, wherein the first and second voltage sources are one or more DC power supplies.

6. The apparatus of claim 3,
    wherein the first switching block comprises:
        a first switch coupled between the first voltage source and the load; and
        a second switch coupled between a first ground and the load,
    wherein the second switching block comprises:
        a third switch coupled between the second voltage source and the load; and
        a fourth switch coupled between a second ground and the load,
    and wherein the controller is configured to control the operation of the first, second, third, and fourth switches such that:
        when the device is to be powered on, the controller alternates engaging each of pairs of first switch and fourth switch, and second switch and third switch to alternatingly couple the load to the first voltage source and the second ground to cause a current flow through the load in a first direction and to the second voltage source and the first ground to cause a current flow through the load in a second direction opposite the first; and
        when the device is to be powered off, the controller alternates engaging each of the pairs of first switch and third switch, and second switch and fourth switch to cause no current to flow through the load.

7. The apparatus of claim 3, wherein the first switching block includes a first inverter, wherein the second switching block includes a second inverter, and wherein the controller controls the operation of the first inverter and the second inverter:
    to power the device on by oscillating the first inverter and the second inverter out of phase to cause current to flow continuously and alternatingly through the load; and
    to power the device off by oscillating the first inverter and the second inverter in phase to cause no current to flow through the load.

8. The apparatus of claim 1, wherein the predetermined carrier frequency is higher than a pass band of an input of a physiological monitor coupled to a patient to which the device is coupled.

9. The apparatus of claim 1, wherein the device is an intravenous fluid warming device, a bypass pump, an infusion pump, or a warming blanket.

10. An apparatus for reducing transient electrical events on a patient monitoring device, comprising:
    a device that is capable of being powered on or off to cause current flow through a load of the device and which is capacitively coupled to a patient during use;
    a first voltage source coupled to a first side of the device through a first switching block;
    a second voltage source coupled to a second side the device opposite the first through a second switching block; and a controller to control the periodic coupling of the first and the second voltage sources to the load out of phase at a predetermined carrier frequency to provide continuous current flow through the load in alternating directions, and to control the periodic coupling of first and second voltage sources to the load in phase at a predetermined carrier frequency to provide no current flow through the load.

11. The apparatus of claim 10, wherein the first voltage source and the second voltage source are provided by a single voltage generator.

12. The apparatus of claim 10, wherein the first and second voltage sources are one or more DC power supplies.

13. The apparatus of claim 10, wherein the predetermined carrier frequency is higher than a pass band of an input of a physiological monitor coupled to a patient to which the device is coupled.

14. The apparatus of claim 10, wherein the device is an intravenous fluid warming device, a bypass pump, an infusion pump, or a warming blanket.

15. The apparatus of claim 10, wherein the first switching block further comprises a first switch coupled between the first voltage source and the load and a second switch coupled between a first ground and the load, wherein the second switching block comprises a third switch coupled between the second voltage source and the load and a fourth switch coupled between a second ground and the load, and wherein the controller is configured to control the operation of the first, second, third, and fourth switches such that when the device is to be powered on, the controller alternates engaging each of pairs of first switch and fourth switch, and second switch and third switch to alternatingly couple the load to the first voltage source and the second ground to cause a current flow through the load in a first direction and to the second voltage source and the first ground to cause a current flow through the load in a second direction opposite the first; and when the device is to be powered off, the controller alternates engaging each of the pairs of first switch and third switch, and second switch and fourth switch to cause no current to flow through the load.

16. The apparatus of claim 10, wherein the first switching block includes a first inverter, wherein the second switching block includes a second inverter, and wherein the controller controls the operation of the first inverter and the second inverter to power the device on by oscillating the first inverter and the second inverter out of phase to cause current to flow continuously and alternatingly through the load; and to power the device off by oscillating the first inverter and the second inverter in phase to cause no current to flow through the load.

17. A method for reducing transients on patient monitoring devices when powering a device having a load that is capacitively coupled to a patient monitoring device, comprising:
periodically coupling a first and a second voltage source to the device out of phase at a predetermined carrier frequency to provide continuous current flow through the load in alternating directions; and
periodically coupling the first and the second voltage sources to the device in phase at a predetermined carrier frequency to provide no current flow through the load.

18. The method of claim 17, wherein the first voltage source and the second voltage source are provided by a single voltage generator.

19. The method of claim 17, wherein the first and the second voltage sources are periodically coupled to the device via a first and a second pair of switches, wherein the two pairs of switches are oscillated out of phase such that a current passes through a load when the device is powered on, and wherein the two pairs of switches are oscillated in phase such that a current does not pass through a load when the device is powered off.

20. The method of claim 17, wherein the first and the second voltage sources are periodically coupled to the device via a first inverter and a second inverter and wherein the first and second inverters are oscillated out of phase to cause current to flow continuously and alternatingly through the load and wherein the first and second inverters are oscillated in phase to cause no current to flow through the load.

21. The method of claim 17, further comprising:
capacitively coupling the device to a patient having a physiological monitor coupled to the patient.

22. The method of claim 21, wherein the physiological monitor possesses a low-pass filter for filtering high frequency transients from an input of the physiological monitor.

23. The method of claim 22, wherein the carrier frequency is greater than an upper frequency limit that is not filtered by the low-pass filter.

* * * * *